(12) United States Patent
Hunt et al.

(10) Patent No.: US 10,166,343 B1
(45) Date of Patent: Jan. 1, 2019

(54) NOISE EVIDENT TAMPER CAP

(71) Applicants: Timothy Brandon Hunt, Hollywood, FL (US); Patrick Vitello, Pompano Beach, FL (US)

(72) Inventors: Timothy Brandon Hunt, Hollywood, FL (US); Patrick Vitello, Pompano Beach, FL (US)

( * ) Notice: Subject to any disclaimer, the term of this patent is extended or adjusted under 35 U.S.C. 154(b) by 13 days.

(21) Appl. No.: 15/069,915

(22) Filed: Mar. 14, 2016

Related U.S. Application Data

(60) Provisional application No. 62/133,075, filed on Mar. 13, 2015.

(51) Int. Cl.
*A61M 5/32* (2006.01)
*A61M 5/50* (2006.01)

(52) U.S. Cl.
CPC ........ *A61M 5/3202* (2013.01); *A61M 5/5086* (2013.01); *A61M 2205/18* (2013.01); *A61M 2205/276* (2013.01)

(58) Field of Classification Search
CPC ............... G11B 27/34; A61M 2205/60; A61M 2205/6063; A61M 5/5086; A61M 5/3202; A61M 2205/18; A61M 2205/276
See application file for complete search history.

(56) References Cited

U.S. PATENT DOCUMENTS

| | | |
|---|---|---|
| 732,662 A | 6/1903 | Smith |
| 1,678,991 A | 7/1928 | Marschalek |
| 1,970,631 A | 8/1934 | Sherman |
| 2,477,598 A | 2/1948 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |

(Continued)

FOREIGN PATENT DOCUMENTS

| | | |
|---|---|---|
| EP | 0148116 A | 7/1985 |
| WO | WO 2017086607 | 5/2015 |

*Primary Examiner* — Brandy S Lee
(74) *Attorney, Agent, or Firm* — Malloy & Malloy, P.L.

(57) ABSTRACT

A noise tamper evident cap assembly for a medical injection device is provided. The assembly includes a sleeve assembly having a sidewall formed circumferentially around a tip cap, and being permanently affixed to a bottom cap. At least one noise fin is formed along an interior of the side wall and disposed in at least partially obstructing and overlying relations relative to a bottom portion of said tip cap, such that the removal of the tip cap will cause an interaction with said noise fin(s) and create an audible indicator. The tip cap is removably connected to the bottom cap via an engagement mechanism, which is also obstructed by the noise fin(s). The bottom cap is structured and dimensioned to enclose a dispensing portion of the medical injection device.

10 Claims, 3 Drawing Sheets

(56) References Cited

U.S. PATENT DOCUMENTS

| | | | |
|---|---|---|---|
| 3,712,749 A | 1/1973 | Roberts | |
| 3,747,751 A | 4/1973 | Miller et al. | |
| 3,872,867 A | 3/1975 | Killinger | |
| 3,905,375 A | 9/1975 | Toyama | |
| 3,937,211 A | 2/1976 | Merten | |
| 4,043,334 A | 8/1977 | Brown et al. | |
| 4,046,145 A | 9/1977 | Choksi et al. | |
| 4,216,585 A | 8/1980 | Hatter | |
| 4,216,872 A | 8/1980 | Bean | |
| 4,244,366 A | 1/1981 | Raines | |
| 4,252,122 A | 2/1981 | Halvorsen | |
| 4,286,591 A | 9/1981 | Raines | |
| 4,313,539 A | 2/1982 | Raines | |
| 4,420,085 A | 12/1983 | Wilson et al. | |
| 4,430,077 A | 2/1984 | Mittleman et al. | |
| 4,457,445 A | 7/1984 | Hanks et al. | |
| 4,521,237 A | 6/1985 | Logothetis | |
| 4,530,697 A | 7/1985 | Kuhlemann et al. | |
| 4,571,242 A | 2/1986 | Klein et al. | |
| 4,589,171 A | 5/1986 | McGill | |
| 4,667,837 A | 5/1987 | Vitello et al. | |
| 4,693,707 A | 9/1987 | Dye | |
| 4,726,483 A | 2/1988 | Drozd | |
| 4,743,229 A | 5/1988 | Chu | |
| 4,743,231 A | 5/1988 | Kay et al. | |
| 4,760,847 A | 8/1988 | Vaillancourt | |
| 4,832,695 A | 5/1989 | Rosenberg et al. | |
| 4,834,706 A | 5/1989 | Beck et al. | |
| 4,844,906 A | 7/1989 | Hermelin et al. | |
| 4,906,231 A | 3/1990 | Young | |
| 4,919,285 A | 4/1990 | Roof et al. | |
| 5,009,323 A | 4/1991 | Montgomery et al. | |
| 5,049,129 A | 9/1991 | Zdeb et al. | |
| 5,051,093 A | 10/1991 | Clegg et al. | |
| 5,135,496 A | 8/1992 | Vetter et al. | |
| 5,165,560 A | 11/1992 | Enniss, III et al. | |
| 5,230,429 A | 7/1993 | Etheredge, III | |
| 5,267,983 A | 12/1993 | Oilschlager et al. | |
| 5,292,308 A | 3/1994 | Ryan | |
| 5,295,599 A | 3/1994 | Smith | |
| 5,328,466 A | 7/1994 | Denmark | |
| 5,328,474 A | 7/1994 | Raines | |
| 5,356,380 A | 10/1994 | Hoekwater et al. | |
| 5,380,295 A | 1/1995 | Vacca | |
| 5,405,339 A | 4/1995 | Kohnen et al. | |
| 5,458,580 A | 10/1995 | Hajishoreh | |
| 5,468,224 A | 11/1995 | Souryal | |
| 5,531,695 A | 7/1996 | Swisher | |
| 5,540,666 A | 7/1996 | Barta et al. | |
| 5,549,571 A | 8/1996 | Sak | |
| 5,558,648 A | 9/1996 | Shields | |
| 5,584,817 A | 12/1996 | van den Haak | |
| 5,588,239 A | 12/1996 | Anderson | |
| 5,624,402 A | 4/1997 | Imbert | |
| 5,674,209 A | 10/1997 | Yarger | |
| 5,700,247 A | 12/1997 | Grimard et al. | |
| 5,702,374 A | 12/1997 | Johnson | |
| 5,776,124 A | 7/1998 | Wald | |
| 5,785,691 A | 7/1998 | Vetter et al. | |
| 5,797,885 A | 8/1998 | Rubin | |
| 5,807,343 A | 9/1998 | Tucker et al. | |
| 5,883,806 A | 3/1999 | Meador et al. | |
| 5,884,457 A | 3/1999 | Ortiz et al. | |
| 5,902,269 A | 5/1999 | Jentzen | |
| 5,951,522 A | 9/1999 | Rosato et al. | |
| 5,951,525 A | 9/1999 | Thorne et al. | |
| 5,954,657 A | 9/1999 | Rados | |
| 5,957,166 A | 9/1999 | Safabash | |
| 5,989,227 A | 11/1999 | Vetter et al. | |
| 6,000,548 A | 12/1999 | Tsals | |
| 6,021,824 A | 2/2000 | Larsen et al. | |
| 6,027,482 A | 2/2000 | Imbert | |
| 6,068,614 A | 5/2000 | Kimber et al. | |
| 6,126,640 A | 10/2000 | Tucker et al. | |
| 6,190,364 B1 | 2/2001 | Imbert | |
| 6,193,688 B1 | 2/2001 | Balestracci et al. | |
| 6,196,593 B1 | 3/2001 | Petrick et al. | |
| 6,196,998 B1 | 3/2001 | Jansen et al. | |
| 6,235,376 B1 | 5/2001 | Miyazaki et al. | |
| 6,280,418 B1 | 8/2001 | Reinhard et al. | |
| 6,287,671 B1 | 9/2001 | Bright et al. | |
| 6,322,543 B1 | 11/2001 | Singh et al. | |
| 6,338,200 B1 | 1/2002 | Baxa et al. | |
| 6,375,640 B1 | 4/2002 | Teraoka | |
| 6,394,983 B1 | 5/2002 | Mayoral et al. | |
| 6,485,460 B2 | 11/2002 | Eakins et al. | |
| 6,500,155 B2 | 12/2002 | Sasso | |
| 6,520,935 B1 | 2/2003 | Jansen et al. | |
| 6,540,697 B2 | 4/2003 | Chen | |
| 6,565,529 B1 | 5/2003 | Kimber et al. | |
| 6,581,792 B1 | 6/2003 | Limanjaya | |
| 6,585,691 B1 | 7/2003 | Vitello | |
| 6,592,251 B2 | 7/2003 | Edwards et al. | |
| 6,682,798 B1 | 1/2004 | Kiraly | |
| 6,726,652 B2 | 4/2004 | Eakins et al. | |
| 6,726,672 B2 | 4/2004 | Hanley et al. | |
| 6,775,220 B2 | 6/2004 | Castellano et al. | |
| 6,764,469 B2 | 7/2004 | Broselow | |
| 6,821,268 B2 | 11/2004 | Balestracci | |
| 6,921,383 B2 | 7/2005 | Vitello | |
| 6,942,643 B2 | 9/2005 | Eakins et al. | |
| 7,055,273 B2 | 6/2006 | Roshkoff | |
| 7,141,286 B1 | 11/2006 | Kessler et al. | |
| 7,182,256 B2 | 2/2007 | Andreasson et al. | |
| 7,240,926 B2 | 7/2007 | Dalle et al. | |
| 7,374,555 B2 | 5/2008 | Heinz et al. | |
| 7,404,500 B2 | 7/2008 | Marteau et al. | |
| 7,410,803 B2 | 8/2008 | Nollert et al. | |
| 7,425,208 B1 | 9/2008 | Vitello | |
| 7,437,972 B2 | 10/2008 | Yeager | |
| 7,482,166 B2 | 1/2009 | Nollert et al. | |
| 7,588,563 B2 | 9/2009 | Guala | |
| 7,594,681 B2 | 9/2009 | DeCarlo | |
| 7,632,244 B2 | 12/2009 | Buehler et al. | |
| 7,641,636 B2 | 1/2010 | Moesli et al. | |
| 7,735,664 B1 | 6/2010 | Peters et al. | |
| 7,748,892 B2 | 7/2010 | McCoy | |
| 7,762,988 B1 | 7/2010 | Vitello | |
| 7,766,919 B2 | 8/2010 | Delmotte | |
| 7,802,313 B2 | 9/2010 | Czajka | |
| 7,918,830 B2 | 4/2011 | Langan et al. | |
| 8,079,518 B2 | 12/2011 | Turner et al. | |
| 8,091,727 B2 | 1/2012 | Domkowski | |
| 8,137,324 B2 | 3/2012 | Bobst | |
| 8,140,349 B2 | 3/2012 | Hanson et al. | |
| 8,257,286 B2 | 9/2012 | Meyer et al. | |
| 8,328,082 B1 | 12/2012 | Bochenko et al. | |
| 8,348,895 B1* | 1/2013 | Vitello | A61M 5/5086 215/253 |
| 8,353,869 B2 | 1/2013 | Ranalletta et al. | |
| 8,443,999 B1 | 5/2013 | Reinders | |
| D684,057 S | 6/2013 | Kwon | |
| 8,512,277 B2 | 8/2013 | Del Vecchio | |
| 8,556,074 B2 | 10/2013 | Turner et al. | |
| 8,579,116 B2 | 11/2013 | Pether et al. | |
| 8,591,462 B1 | 11/2013 | Vitello | |
| 8,597,255 B2 | 12/2013 | Emmott et al. | |
| 8,597,271 B2 | 12/2013 | Langan et al. | |
| 8,616,413 B2 | 12/2013 | Koyama | |
| D701,304 S | 3/2014 | Lair et al. | |
| 8,672,902 B2 | 3/2014 | Ruan et al. | |
| 8,702,674 B2 | 4/2014 | Bochenko | |
| 8,777,930 B2 | 7/2014 | Swisher et al. | |
| 8,852,561 B2 | 10/2014 | Wagner et al. | |
| 8,864,021 B1 | 10/2014 | Vitello | |
| 8,864,707 B1 | 10/2014 | Vitello | |
| 8,864,708 B1 | 10/2014 | Vitello | |
| 8,945,082 B2 | 2/2015 | Geiger et al. | |
| 9,101,534 B2 | 8/2015 | Bochenko | |
| 9,199,042 B2 | 12/2015 | Farrar et al. | |
| 9,199,749 B1 | 12/2015 | Vitello | |
| 9,220,486 B2 | 12/2015 | Schweiss et al. | |
| 9,220,577 B2 | 12/2015 | Jessop et al. | |
| 9,272,099 B2 | 3/2016 | Limaye et al. | |

(56) References Cited

U.S. PATENT DOCUMENTS

| | | | |
|---|---|---|---|
| 9,311,592 B1 | 4/2016 | Vitello | |
| D756,777 S | 5/2016 | Berge et al. | |
| 9,336,669 B2 | 5/2016 | Bowden et al. | |
| D759,486 S | 6/2016 | Ingram et al. | |
| 9,402,967 B1 | 8/2016 | Vitello | |
| 9,427,715 B2 | 8/2016 | Palazzolo et al. | |
| 9,433,768 B2 | 9/2016 | Tekeste et al. | |
| 9,463,310 B1 | 10/2016 | Vitello | |
| D773,043 S | 11/2016 | Insgram et al. | |
| D789,529 S | 6/2017 | Davis et al. | |
| 9,687,249 B2 | 6/2017 | Hanlon et al. | |
| D797,928 S | 9/2017 | Davis et al. | |
| D797,929 S | 9/2017 | Davis et al. | |
| 9,855,191 B1 | 1/2018 | Vitello | |
| D815,945 S | 4/2018 | Fischer et al. | |
| D825,746 S | 8/2018 | Davis et al. | |
| 2001/0034506 A1 | 10/2001 | Hirschman | |
| 2001/0056258 A1 | 12/2001 | Evans | |
| 2002/0023409 A1 | 2/2002 | Py | |
| 2002/0099334 A1 | 7/2002 | Hanson | |
| 2002/0101656 A1 | 8/2002 | Blumenthal | |
| 2002/0133119 A1 | 9/2002 | Eakins et al. | |
| 2003/0146617 A1 | 8/2003 | Franko, Sr. | |
| 2003/0183547 A1 | 10/2003 | Heyman | |
| 2004/0064095 A1 | 4/2004 | Vitello | |
| 2004/0116858 A1 | 6/2004 | Heinz et al. | |
| 2004/0186437 A1 | 9/2004 | Frenette et al. | |
| 2004/0225258 A1 | 11/2004 | Balestracci | |
| 2005/0146081 A1 | 7/2005 | MacLean et al. | |
| 2005/0148941 A1 | 7/2005 | Farrar et al. | |
| 2005/0209555 A1 | 9/2005 | Middleton et al. | |
| 2006/0084925 A1 | 4/2006 | Ramsahoye | |
| 2006/0089601 A1 | 4/2006 | Dionigi | |
| 2006/0173415 A1 | 8/2006 | Cummins | |
| 2006/0189933 A1 | 8/2006 | Alheidt | |
| 2007/0060898 A1 | 3/2007 | Shaughnessy et al. | |
| 2007/0106234 A1 | 5/2007 | Klein | |
| 2007/0142786 A1 | 6/2007 | Lampropoulos et al. | |
| 2007/0191690 A1 | 8/2007 | Hasse | |
| 2007/0219503 A1 | 9/2007 | Loop | |
| 2007/0257111 A1 | 11/2007 | Ortenzi | |
| 2008/0068178 A1 | 3/2008 | Meyer | |
| 2008/0097310 A1* | 4/2008 | Buehler | A61M 5/50 604/111 |
| 2008/0106388 A1 | 5/2008 | Knight | |
| 2008/0243088 A1 | 10/2008 | Evans | |
| 2008/0306443 A1 | 12/2008 | Neer | |
| 2009/0099552 A1 | 4/2009 | Levy et al. | |
| 2009/0149815 A1 | 6/2009 | Kiel et al. | |
| 2009/0326481 A1 | 12/2009 | Swisher et al. | |
| 2010/0084403 A1 | 4/2010 | Popish et al. | |
| 2010/0126894 A1 | 5/2010 | Koukol et al. | |
| 2010/0179822 A1 | 7/2010 | Reppas | |
| 2010/0228226 A1 | 9/2010 | Nielsen | |
| 2010/0252564 A1 | 10/2010 | Martinez et al. | |
| 2010/0283238 A1 | 11/2010 | Deighan et al. | |
| 2011/0044850 A1 | 2/2011 | Solomon et al. | |
| 2011/0046550 A1 | 2/2011 | Schiller et al. | |
| 2011/0046603 A1 | 2/2011 | Felsovalyi et al. | |
| 2012/0064515 A2 | 3/2012 | Knapp et al. | |
| 2012/0096957 A1 | 4/2012 | Ochman | |
| 2012/0110950 A1 | 5/2012 | Schraudolph | |
| 2013/0018356 A1 | 1/2013 | Prince et al. | |
| 2013/0088354 A1 | 4/2013 | Thomas | |
| 2013/0237949 A1 | 9/2013 | Miller | |
| 2014/0000781 A1 | 1/2014 | Franko, Jr. | |
| 2014/0034536 A1 | 2/2014 | Reinhardt et al. | |
| 2014/0069829 A1 | 3/2014 | Evans | |
| 2014/0135738 A1 | 5/2014 | Panian | |
| 2014/0155868 A1 | 6/2014 | Nelson et al. | |
| 2014/0257843 A1 | 9/2014 | Adler et al. | |
| 2014/0326727 A1 | 11/2014 | Jouin | |
| 2014/0353196 A1 | 12/2014 | Key | |
| 2015/0191633 A1 | 7/2015 | De Boel et al. | |
| 2015/0305982 A1 | 10/2015 | Bochenko | |
| 2015/0310771 A1 | 10/2015 | Atkinson et al. | |
| 2016/0067422 A1 | 3/2016 | Davis et al. | |
| 2016/0090456 A1 | 3/2016 | Ishimaru | |
| 2016/0144119 A1 | 5/2016 | Limaye et al. | |
| 2016/0158110 A1 | 6/2016 | Swisher et al. | |
| 2016/0158449 A1 | 6/2016 | Limaye et al. | |
| 2016/0176550 A1 | 6/2016 | Vitello et al. | |
| 2016/0328586 A1 | 11/2016 | Bowden et al. | |
| 2016/0361235 A1 | 12/2016 | Swisher | |
| 2016/0367439 A1 | 12/2016 | Davis et al. | |
| 2017/0014310 A1 | 1/2017 | Hyun et al. | |
| 2017/0124289 A1 | 5/2017 | Hasan | |
| 2017/0173321 A1 | 6/2017 | Davis et al. | |
| 2017/0203086 A1 | 7/2017 | Davis | |
| 2017/0319438 A1 | 11/2017 | Davis et al. | |
| 2018/0001540 A1 | 1/2018 | Byun | |
| 2018/0089593 A1 | 3/2018 | Patel et al. | |

* cited by examiner

NOISE EVIDENT TAMPER CAP

CLAIM OF PRIORITY

This application claims priority to U.S. provisional patent application having Ser. No. 62/133,075, filed on Mar. 13, 2015, which is herein incorporated by reference in its entirety.

BACKGROUND OF THE INVENTION

Field of the Invention

The present invention is directed to a noise tamper evident cap assembly for use with a medical injection or dispensing device such as a syringe. Specifically, the assembly of the present invention provides for the bottom loading of a tip cap to the assembly, an audible noise indication is triggered upon separation of the tip cap and the sleeve, and the tip cap cannot be reversed back into the assembly.

Description of the Related Art

It is common practice for medical personnel to provide a patient with a drug or medication by injection, and a top concern in the medical field relates to the safety of administration of these injections. Another common concern relates to the anti-theft of these types of injections by medical personnel. Accordingly, it would be advantageous to provide an anti-tamper cap assembly to medical syringes or dispensing devices, which also provides an audible indicator upon use, to ensure that the syringe has been opened and/or used, rather than pocketed.

SUMMARY OF THE INVENTION

The present invention is directed to a noise tamper evident cap assembly which may include a sleeve assembly, a tip cap, and a bottom cap. The sleeve assembly is formed in surrounding relations to the tip cap, and includes one or more noise fin(s) that are formed along an interior wall or sidewall of the sleeve assembly, and disposed upwards and in overlying relations relative to the tip cap. The tip cap is removably connected to the bottom cap, and the bottom cap may be permanently affixed to a medical syringe as well as the sleeve assembly. Upon removal of the tip cap, a portion thereof, such as its engagement flange, may interact with or touch upon the noise fin(s), cause the fin(s) to vibrate and emit an audible noise or tone with a human hearing range.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As shown in the accompanying Figures, the present invention is directed to a noise tamper evident cap assembly, generally indicated as 100, for use with a medical injection device such as a syringe and including a noise feature.

Figure 3:
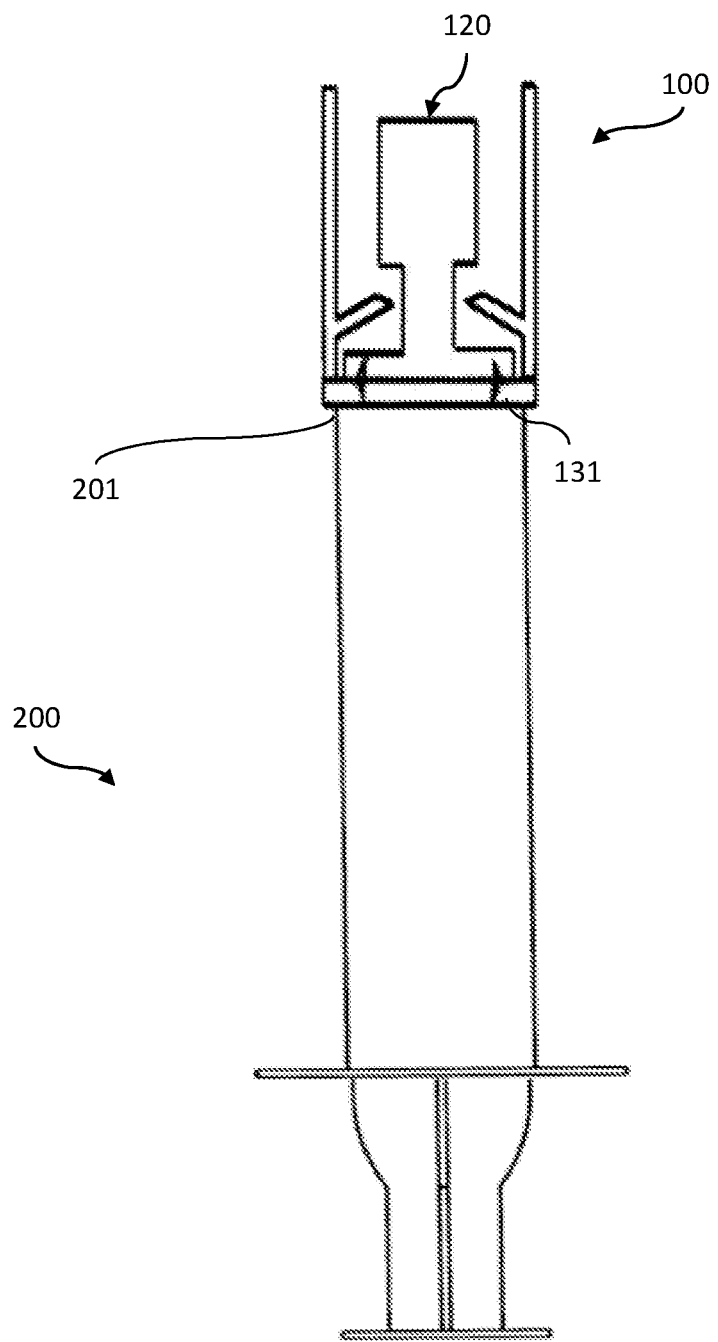
FIG. 3 is a schematic side profile representation of an assembled noise tamper evident cap assembly in use with a medical syringe.

As seen in FIG. 3, the assembly 100 is intended to be used as a closure with a syringe 200, such as to enclose an apical portion or dispensing portion 201 of the syringe 200.

Figure 2:
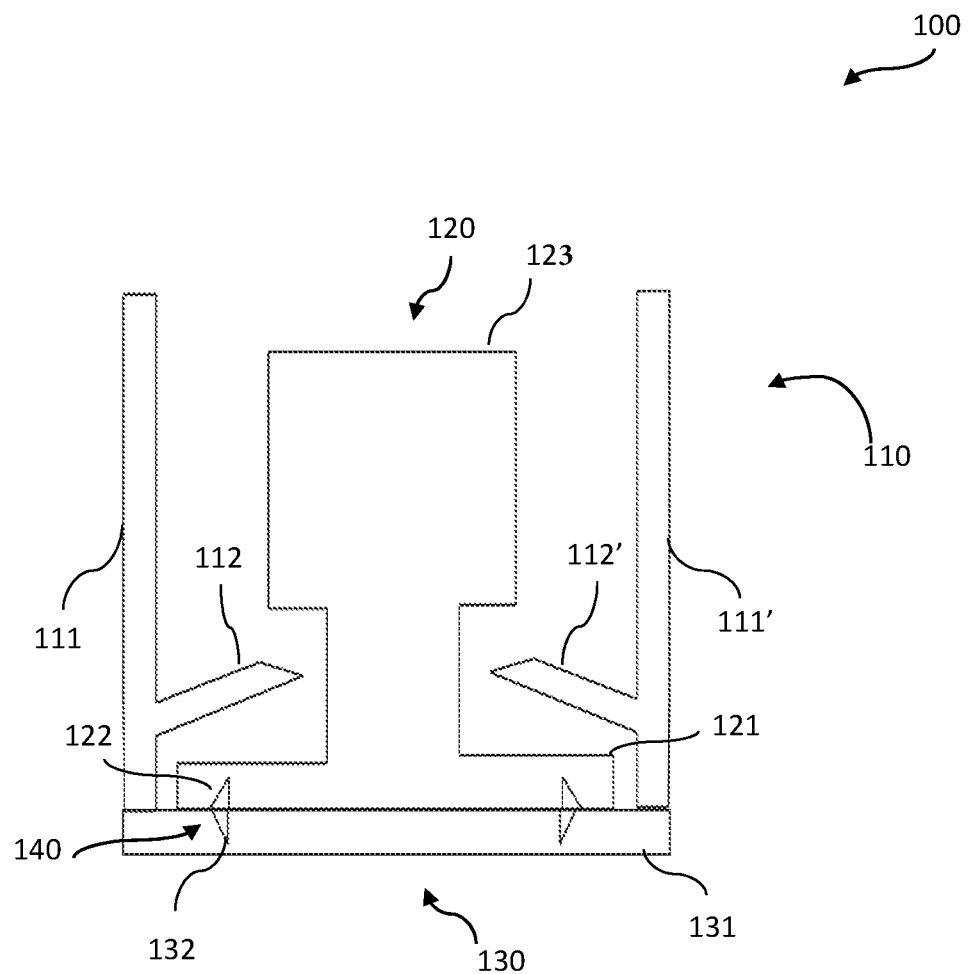
FIG. 2 is a schematic side profile view representation of a noise tamper evident cap assembly of the present invention, assembled.

Drawing attention to FIG. 2, a cross section and/or side profile of the present invention is presented in assembled form. Accordingly, the assembly 100 of the present invention may generally and initially comprise three primary components, including a sleeve assembly 110, a tip cap 120, and a bottom cap 130.

The sleeve assembly 110 comprises at least one side wall 111. The sidewall 111 may form circumferentially atop the bottom cap 130, and around the tip cap 120, as a one piece construction. In other embodiments, the side wall 111 may comprise one or more side wall segments such as 111 and 111' formed on different sections and in surrounding relations to the tip cap 120.

The sleeve assembly 110 and side wall 111 further comprises at least one noise fin 112 and/or 112' protruding into an interior of said side wall 111. This at least one noise fin 112 and/or 112' is disposed in at least partially obstructing relations relative to the tip cap 120, such that the removal of the tip cap 120 will cause a bottom portion of the tip cap 120, or more specifically, the engagement flange 121 thereof, to interact with the noise fin(s) 112/112', which in turn causes air vibrations and result in a "snap" or "click" sound, as an audio indicator to the user and/or surrounding personnel proximal to the user, that the cap has been removed.

The noise fins 112/112' may be angled upwards at varying degrees, relative to the base or bottom of the medical injection device, such that the tip cap 120 is unable to pass back through the noise fins 112/112' after removal. Further, the noise fins 112/112' will be partial or full obstructive relations relative to the engagement members 122 and 132, which means that the engagement flange 121 of the tip cap 120 will be unable to connect back to the bottom cap 130.

The noise fin(s) 112/112' may be formed of at least partially flexible materials including known plastics, metals, and/or other appropriate materials for producing an audible sound or tone to the human ear, or a vibrational sound between the 20 Hz and 20 kHz range. The noise fin(s) 112/112' may form of a single construction as the sidewall 111 and/or segments thereof. Or, in one embodiment, the noise fin(s) 112/112' may be attached by ultrasonic welding, clipping, or gluing via adhesives.

The tip cap 120 may comprise a shape that may facilitate its removal, such as to include a head member 123 that may facilitate a user's grip for removal of the tip cap 120. In this way, the tip cap 120 may be removed from the sleeve assembly 110 without breaking any tabs, and thereby reducing particle generation and increasing manufacturability. The absence of the sleeve assembly 110 and/or a segment thereof may indicate that the cap assembly 100 has been tampered with.

The sleeve assembly 110 may be permanently affixed to the bottom cap 130, via adhesives, welding, and/or other appropriate means. The bottom cap 130 may similarly be permanently affixed to an apical portion of the medical injection device or syringe 200. In one embodiment, the bottom cap 130 may comprise an aperture for dispensing or access to the fluids or content within the syringe 200, after removal of the tip cap 120. In one embodiment, access for removal of the bottom cap 130, which serves as a closure or lid to the syringe 200, may only be achieved after the removal of the tip cap 120. For example, the bottom cap 130 may incorporate therein the closure device as taught in Applicant's invention in issued U.S. Pat. No. 8,886,021, which is incorporated herein in its entirety.

The assembly of the present invention may be introduced for both male and female gendered threaded connectors of all types related to a syringe or other medical injection or dispensing device, and may include pipe thread, inch and metric thread and taps, in addition to the leur, enteral, and neuraxial thread standards.

Figure 1:
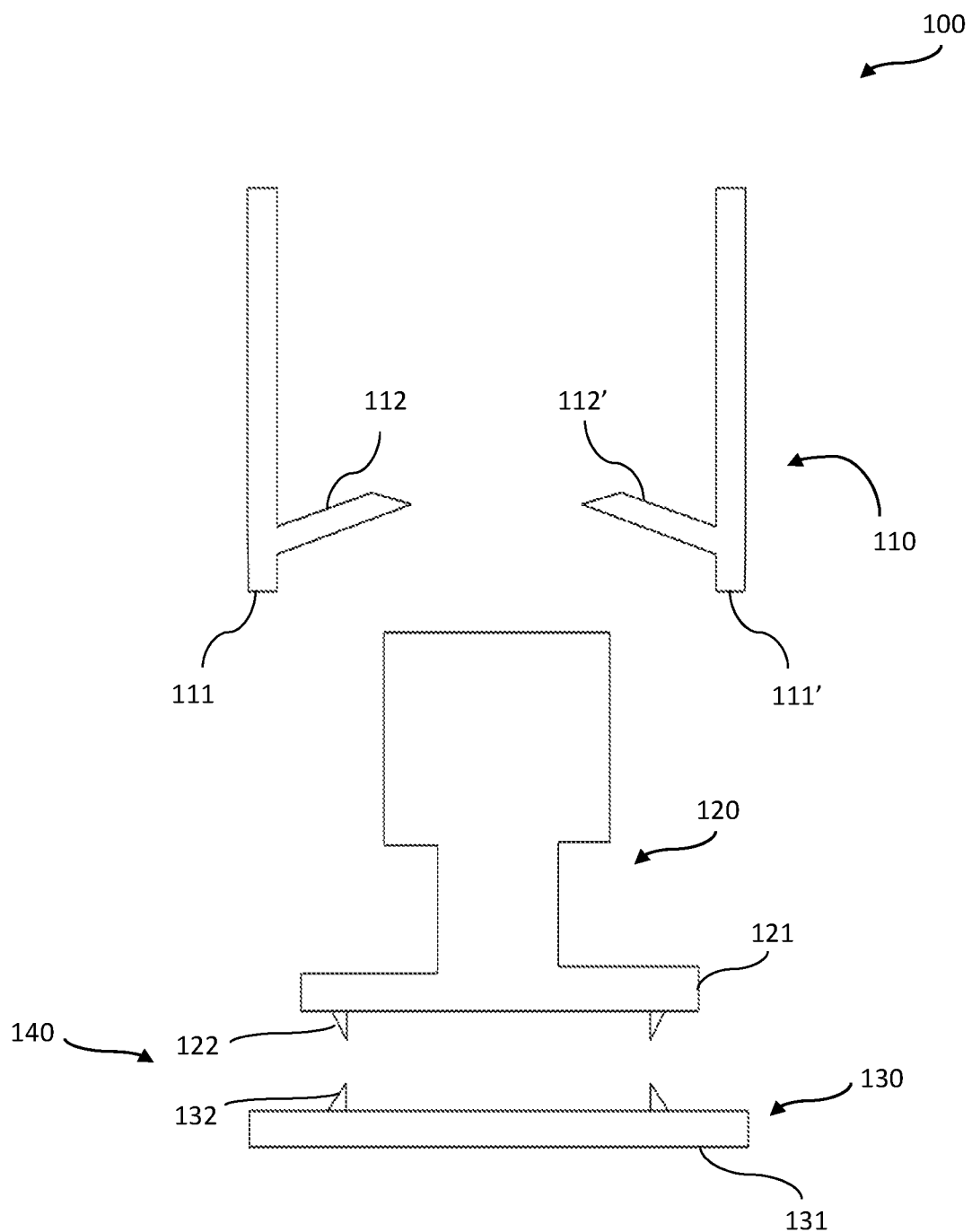
FIG. 1 is a schematic side profile view representation of a noise tamper evident cap assembly of the present invention, pre-assembled.

Drawing attention to FIG. 1, the construction of the assembly 100 may involve a "bottom loaded" approach. That is, the tip cap 120 is inserted upwards into the sleeve assembly 110, and the bottom cap 130 is connected to the tip cap 120 via an engagement mechanism 140, which may include the cooperative engagement of at least engagement members 122 and 132, followed by the permanent welding or adhesion of the bottom cap 130 with the sleeve assembly 110 and/or the sidewalls 111 or sidewall segments 111/111' thereof. The engagement mechanism 140 and engagement members 122 and 132 cooperatively formed on the engagement flange 121 of the tip cap 120, and the engagement member of the bottom cap 130, may comprise a standard "cliff and ramp" mechanism for installation, with each engagement member or connector being an opposite gender of the opposing.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described, What is claimed is:

1. A noise tamper evident cap assembly for a medical injection device comprising:
   a sleeve assembly comprising at least one side wall, said side wall forming circumferentially around a tip cap, and being permanently affixed to a bottom cap,
   at least one noise fin formed along an interior of said at least one side wall, and disposed in at least partially obstructing and overlying relations relative to a bottom portion of said tip cap,
   said tip cap being removably connected to said bottom cap via an engagement mechanism, said bottom portion of said tip cap interacting with said at least one noise fin upon removal of said tip cap from said sleeve assembly creating an audio indicator to a user, and
   said bottom cap structured and dimensioned to enclose a dispensing portion of the medical injection device.

2. The noise tamper evident cap assembly of claim 1 wherein said noise fin(s) are structured and configured to vibrate the surrounding air in order to create an audible indicator, upon the removal of said tip cap from said bottom cap.

3. The noise tamper evident cap assembly of claim 1 wherein said tip cap further comprises an engagement flange that cooperative engages with said bottom cap via said engagement mechanism.

4. The noise tamper evident cap assembly of claim 3 wherein said engagement mechanism comprises the removable engagement of least one tip cap engagement member with at least one bottom cap engagement member.

5. The noise tamper evident camp assembly of claim 3 wherein said noise fin(s) are structured and configured to vibrate the surrounding air in order to create an audible indicator, upon the resulting interaction between said engagement flange and said at least one noise fin.

6. The noise tamper evident cap assembly of claim 1 wherein said bottom cap is permanently affixed to an apical portion of the medical injection device.

7. The noise tamper evident cap assembly of claim 1 wherein said noise fins are angled upwards relative to a base of the medical injection device, such that said tip cap is unable to pass back through said noise fins after removal.

8. The noise tamper evident cap assembly of claim 7 wherein said noise fins are structured and configured in at least partially obstructive relations relative to a portion of said engagement mechanism formed on said bottom cap.

9. The noise tamper evident cap assembly of claim 7 wherein said noise fins are structured and configured in fully obstructive relations relative to a portion of said engagement mechanism formed on said bottom cap.

10. A noise tamper evident cap assembly for a medical injection device comprising:
    a sleeve assembly comprising a side wall formed circumferentially in surrounding relations relative to a tip cap, and being permanently affixed to a bottom cap
    said side wall including at least one noise fin protruding along an interior thereof, and disposed in an upward angle,
    said at least one noise fin further disposed in at least partially obstructing relations relative to an engagement flange of said tip cap,
    said tip cap being removably connected to said bottom cap via an engagement mechanism, and
    said bottom cap structured and dimensioned to enclose a dispensing portion of the medical injection device.

* * * * *